(12) United States Patent
Lijoi et al.

(10) Patent No.: US 12,239,495 B2
(45) Date of Patent: Mar. 4, 2025

(54) SURGICAL SKIN MARKER

(71) Applicant: DaVinci Plastic Surgery, PC, Washington, DC (US)

(72) Inventors: Katherine Lynn-Long Lijoi, Arlington, VA (US); Steven Davison, Washington, DC (US)

(73) Assignee: DaVinci Plastic Surgery, PC, Washington, DC (US)

( * ) Notice: Subject to any disclaimer, the term of this patent is extended or adjusted under 35 U.S.C. 154(b) by 0 days.

(21) Appl. No.: 18/217,146

(22) Filed: Jun. 30, 2023

(65) Prior Publication Data

US 2025/0000606 A1    Jan. 2, 2025

(51) Int. Cl.
  *A61B 90/00*    (2016.01)
  *B43K 8/02*    (2006.01)
  *B43K 8/03*    (2006.01)
  *B43K 23/08*    (2006.01)

(52) U.S. Cl.
  CPC .............. *A61B 90/39* (2016.02); *B43K 8/024* (2013.01); *B43K 8/03* (2013.01); *B43K 23/08* (2013.01); *A61B 2090/395* (2016.02)

(58) Field of Classification Search
  CPC .... A61B 2090/395; B43K 1/006; B43K 1/12; B43K 8/24
  USPC .................................................. 401/116, 202
  See application file for complete search history.

(56) References Cited

U.S. PATENT DOCUMENTS

| | | | | |
|---|---|---|---|---|
| 4,538,612 A | * | 9/1985 | Patrick, Jr. | A61B 5/325 15/207.2 |
| 6,551,265 B1 | * | 4/2003 | Miguel | B43K 8/003 604/1 |
| 8,152,401 B2 | * | 4/2012 | Sokoloff | A61B 90/39 401/198 |
| 8,303,202 B1 | * | 11/2012 | Garcia | B43L 19/0056 434/85 |
| 9,815,317 B2 | * | 11/2017 | Bezuhly | B43K 1/12 |
| 2008/0287782 A1 | * | 11/2008 | Traboulsi | A61B 90/39 600/426 |

* cited by examiner

*Primary Examiner* — David P Angwin
*Assistant Examiner* — Bradley S Oliver
(74) *Attorney, Agent, or Firm* — Cooley LLP

(57) ABSTRACT

The invention encompasses a sterile skin marker whose felt ink reservoir can be advanced by twisting the end of the marker revealing additional felt tip. The dried portion of the previously used felt tip can be cut off to reveal a fresh, ink saturated felt tip.

8 Claims, 3 Drawing Sheets

SURGICAL SKIN MARKER

FIELD OF THE INVENTION

The invention encompasses a sterile skin marker whose felt ink reservoir can be advanced by twisting the end of the marker revealing additional felt tip. The dried portion of the previously used felt tip can be cut off to reveal a fresh, ink saturated felt tip.

BACKGROUND OF THE INVENTION

Prior technology includes surgical skin markers that must be disposed of after short-term use with much of the felt-reservoir still saturated with ink. This is due to the nature of the felt tip to stop producing ink after short-term use due to contaminating contact with, for example, betadine or due to the fact that the ink in the exposed tip has simply dried up. For these reasons, multiple sterile skin markers must be utilized for each surgical case.

SUMMARY OF THE INVENTION

The invention encompasses a multi-use felt tip surgical marker.

In embodiments, the invention encompasses a felt marking pen comprising: a shaft cylinder; a porous felt tip core accommodated in the shaft cylinder, a felt ink reservoir, an indicator notch on the felt tip, and an advancing rotary, which is configured to be able to project from and retract into an opening part provided at a tip end of the shaft cylinder; an inner area including an advancing rotary accommodated in the shaft cylinder, and filled with an ink composition to be fed to the pen core. In certain embodiments, the ink is an aqueous ink composition including a water soluble solvent, and a delivery mechanism configured to cause a tip end of the pen core to project from and retract into the opening part.

In certain embodiments, the felt ink tip includes a plurality of notches with indicator marks that can be cut for multiple use.

In certain embodiments, due to a solvent being included in an aqueous medium, the affinity between the aqueous ink composition and the inner felt is increased. Due to the increase of the affinity between the aqueous ink and the inner felt, the force by which the inner cotton retains the aqueous ink composition increases, and this retaining force resists the impact of landing and prevents the aqueous ink composition from splattering.

In certain embodiments, the structure of the felt marker, in a state in which the tip end of the pen core has been retracted into the shaft cylinder, the tip end is positioned rearward from the opening part by, for example, 1 mm or more. In other embodiments, the marker includes a screw at the end of the pen and advancement track, wherein when the screw is turned the felt tip is advanced, for example, by 1 mm or more.

In other embodiments, the invention encompasses a surgical marker comprising (i) external portion comprising an outer shaft casing, a cap, an indicator notch, and an advancing rotary, and an (ii) an internal portion comprising a felt ink reservoir, an internal screw, an advancement track, and a felt ink reservoir advancing base, wherein in the felt ink reservoir includes one or more notches that can be cut for multiple use.

In certain embodiments, the felt marker is included in a sterile packaging for surgical use.

The invention also encompasses the use of the surgical marker for surgical planning of a human or animal comprising: removing the marker from the sterile packaging, uncapping the marker, advancing the felt ink reservoir, using the skin marker to draw on a patient's skin to outline a surgical plan, when the marker no longer produces ink (either because the tip has dried or because betadine has impeded the flow of ink), twisting the advancing rotary on the marker's end opposite the ink tip, advancing the felt ink reservoir, for example about ½ cm (e.g., one notched segment) so that approximately 1 cm of felt ink reservoir (e.g., two notched segments) are exposed past the skin marker's outer casing, utilizing a pair of surgical scissors (e.g., surgical mayo scissors) cut the end of the felt ink reservoir off at the exposed notch leaving ½ cm of ink-saturated felt ink reservoir exposed, continue to utilized the skin marker for general surgical planning, and repeating the steps as needed.

In certain embodiments, the invention encompasses a reusable, surgical felt tip marker comprising:
 (i) an external portion comprising:
   (a) an outer casing;
   (b) a cap;
   (c) a felt ink reservoir comprising one or more indicator notches; and
   (d) an advancing rotary; and
 (ii) an internal portion comprising:
   (a) an internal screw;
   (b) an advancement track; and
   (c) a felt ink reservoir advancing base.

In certain embodiments, the felt ink reservoir is sterile for use in surgical procedures.

In certain embodiments, the surgical felt tip marker is included within sterile packaging.

In certain embodiments, the surgical felt tip marker includes an advancing rotary, which is a combination of:
 a user operated tip rotator mounted in end cap of a hollow body,
 an internal screw;
 an advancing track; and
 a felt ink reservoir advancing base.

In certain embodiments, the invention encompasses a method of pre-operative surgical planning of a subject comprising:
 removing the reusable, surgical felt tip marker of claim 1 from a sterile packaging,
 uncapping the marker,
 advancing the felt ink reservoir,
 using the skin marker to draw on a subject's skin to outline a surgical plan,
 when the marker no longer produces ink, twisting the advancing rotary on the marker's end opposite the ink tip, advancing the felt ink reservoir about ½ cm (e.g., one notched segment) so that approximately 1 cm of felt ink reservoir (e.g., two notched segments) are exposed past the skin marker's outer casing, utilizing a pair of surgical scissors (e.g., surgical mayo scissors) cut the end of the felt ink reservoir off at the exposed notch leaving ½ cm of ink-saturated felt ink reservoir exposed, continue to utilized the skin marker for general surgical planning, and repeating as needed.

In certain embodiments, the subject is a human.
In certain embodiments, the subject is an animal.

DETAILED DESCRIPTION OF THE INVENTION

Figure 1:
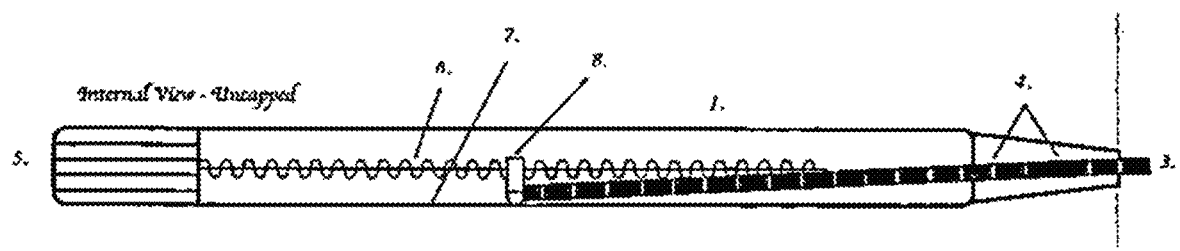
FIG. 1 is a front internal view of a felt marking pen of an embodiment of the present application, and illustrates a state in which a tip end of a pen uncapped.
Figure 2:
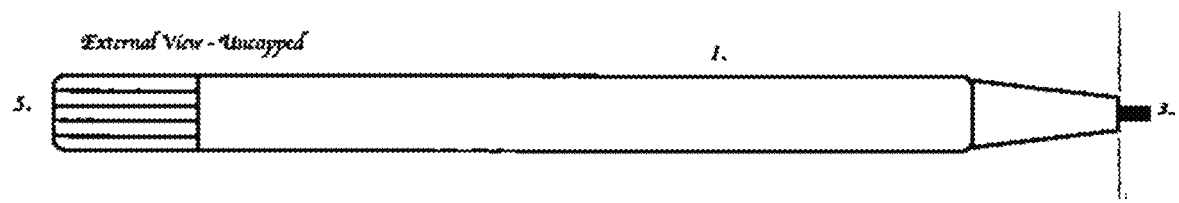
FIG. 2 is an external uncapped view.

An embodiment of the present application is described hereinafter with reference to the drawings. In the following description, the side of a surgical skin marker at which side a felt ink reservoir (i.e., a writing tip end) 3 is positioned is referred to as the tip end side, and the side opposite thereto is referred to as the advancing rotary 5, which is at a rear end side. Further, the direction heading toward the tip end side is referred to as the frontward direction, and the direction opposite thereto is referred to as the rearward direction. Moreover, in cases in which identical reference numerals are used in different drawings, the identical reference numerals indicate identical structures even if the structures indicated by the reference numerals are not referenced per drawing.

Figure 3:
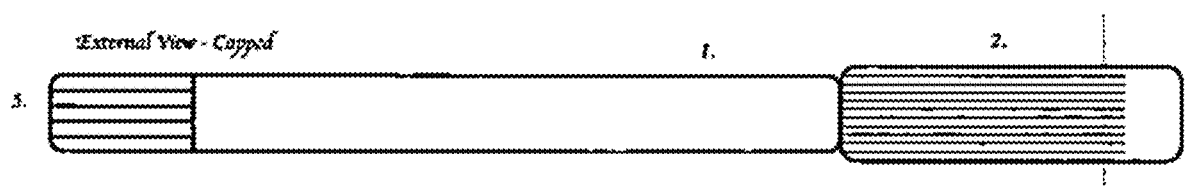
FIG. 3 is an external capped view.

FIG. 1 illustrates a state in which, at the surgical felt marker of the embodiment of the present application, the felt ink reservoir 3 that is the tip end of a pen core has been extended from the internal reservoir. As illustrated in the internal view of FIG. 1 the felt ink reservoir has, at the tip end side of a shaft cylinder that is cylindrical tube shaped, a tip end reduced-diameter portion whose outer diameter gradually decreases toward the front side, and has a end portion that is attached to the rear end of the shaft cylinder, an advancing rotary 5 projects out from the end portion and extends forward, and includes a twistable rotating portion that allows advancement of the felt ink reservoir. An opening part is formed at the tip end of the tip end reduced-diameter portion, wherein the felt ink reservoir can be advanced to allow surgical marking of a subject. The reduced diameter portion can be covered with a cap and serves as a protection of the felt ink reservoir as illustrated in the view of FIG. 3.

As illustrated in FIG. 1 that is internal, cross-sectional view of the surgical skin marker, an ink accommodating felt ink reservoir 3, which is tubular and at whose tip end is felt and can be cut and removed for additional use and is housed at the interior of the shaft cylinder of the surgical marking pen. Inner felt that is formed from, for example, wool, viscose, polyester, polypropylene, nylon, or cotton fibers is accommodated at the interior of the ink accommodating felt ink reservoir. The tip end side of the felt ink reservoir is located in the cylindrical accommodating tube which outer diameter is reduced. The felt ink reservoir optionally includes one or more notches 4.

A core or internal portion of the surgical marker, which is shaped as a solid cylinder and which includes an internal screw 6 connected to an advancement track 7, and a felt ink reservoir advancing base 8, allows advancement of the felt ink reservoir through the end with rotation of the advancing rotary.

The ink composition of the felt ink reservoir can include an aqueous ink composition includes a water soluble solvent in an amount of from 10 mass % to 80 mass %, preferably from 20 mass % to 60 mass %, and more preferably from 30 mass % to 50 mass %. This water soluble solvent is not particularly limited provided that it is an organic solvent having a hydrophobic group and a hydrophilic group in the molecule structure, and an organic compound having two or more, and preferably two or three, hydroxy groups (—OH) within the molecule is preferable. Examples of such an organic compound are glycerin, diethylene glycol, triethylene glycol, propylene glycol, and ethylene glycol. Inclusion of such a water soluble organic solvent improves the affinity of the aqueous ink composition with respect to the inner felt ink reservoir.

Further, it is preferable that a felt ink reservoir at the tip end of the pen core can be cut in order to prevent drying or dirtying due to the adhesion of ink, and once cut can be used for further surgical procedures on the same or a different subject. The subject can be a human or an animal. Further, it is preferable for the aqueous ink composition to have the initial viscosity at shear rates of 1 to 383 s−1 (25° C.) within the range of 2 to 15 mPa·sec, and the surface tension (25° C.) greater than or equal to 30 mN/m.

An end cap 2 that is substantially shaped as a cylindrical tube is press-fit into and fixed to the end side covering the felt ink reservoir.

A delivery mechanism 5 is formed by the advancing rotary 5. As will be described later, this advancing rotary 5 causes the felt ink reservoir 3 to project out from and retract into the opening part. An internal screw 6 that is placed in the pen core is interposed between a rear end, which is positioned at the rear end edge of the pen core of the tube, and a tip end, which is a step formed at the inner peripheral surface of the tip end reduced-diameter portion of the shaft cylinder. The advancing rotary urges the felt ink reservoir 3 toward the tip end reduced-diameter portion.

The pen core is formed in the shape of a rod having a circular cross-section. The tip end side of the pen core is the felt ink reservoir 3 that is formed in a substantially hemispherical shape. The rear end side of the pen core includes the advancing rotary 5.

It should be understood that the foregoing description is only illustrative of the invention. Various alternatives and modifications can be devised by those skilled in the art without departing from the invention. Accordingly, the present invention in intended to embrace all such alternatives, modifications and variances that fall within the scope of the appended claims.

What is claimed is:

1. A method of pre-operative surgical planning of a subject comprising:
   removing a reusable, surgical felt tip marker from a sterile packaging,
   uncapping the marker,
   advancing the felt ink reservoir,
   using the skin marker to draw on a subject's skin to outline a surgical plan,
   when the marker no longer produces ink, twisting the advancing rotary on the marker's end opposite the ink tip, advancing the felt ink reservoir about ½ cm so that approximately 1 cm of felt ink reservoir are exposed past the skin marker's outer casing, cutting the end of the felt ink reservoir off leaving about ½ cm of ink-saturated felt ink reservoir exposed, to continue to utilized the skin marker for general surgical planning, and repeating as needed,
   wherein the reusable, surgical felt tip marker comprises:
   (i) an external portion comprising:
      (a) an outer casing;
      (b) a felt ink reservoir comprising one or more indicator notches; and
      (c) an advancing rotary; and
   (ii) an internal portion comprising:
      (a) an internal screw;
      (b) an advancement track; and
      (c) a felt ink reservoir advancing base.

2. The method of claim 1, wherein the subject is a human.

3. The method of claim 1, wherein the subject is an animal.

4. The method of claim 1, wherein the felt ink reservoir is sterile for use in surgical procedures.

5. The method of claim 1, wherein the advancing rotary further comprises a user operated tip rotator mounted in an end cap of a hollow body.

6. The method of claim 1, wherein the advancing the felt ink reservoir about ½ cm corresponds to an advance of one notched segment.

7. The method of claim 1, wherein the advancing the felt ink reservoir about 1 cm corresponds to an advance of two notched segments.

8. The method of claim 1, wherein the cutting the end of the felt ink reservoir is done using a pair of surgical scissors to remove the tip that no longer produces ink.

* * * * *